United States Patent
Kakuuchi et al.

(10) Patent No.: US 6,805,443 B2
(45) Date of Patent: Oct. 19, 2004

(54) OPHTHALMIC APPARATUS

(75) Inventors: Atsushi Kakuuchi, Hamamatsu (JP);
Shigeru Takimoto, Hamamatsu (JP);
Tadashi Ichihashi, Tokyo (JP)

(73) Assignee: Kowa Company Ltd., Nagoya (JP)

( * ) Notice: Subject to any disclaimer, the term of this patent is extended or adjusted under 35 U.S.C. 154(b) by 0 days.

(21) Appl. No.: 10/298,710

(22) Filed: Nov. 18, 2002

(65) Prior Publication Data

US 2004/0095555 A1 May 20, 2004

(51) Int. Cl.$^7$ .................................................. A61B 3/10
(52) U.S. Cl. .................................................... 351/214
(58) Field of Search ................................... 351/201, 205, 351/208, 214, 221, 245, 206; 359/362, 368, 374–385; 600/556, 558

(56) References Cited

U.S. PATENT DOCUMENTS 5,735,283 A * 4/1998 Snook ......................... 600/558
6,208,460 B1 * 3/2001 Degenhardt et al. ........ 359/385
6,361,167 B1 * 3/2002 Su et al. ...................... 351/206

* cited by examiner

Primary Examiner—George Manuel
(74) Attorney, Agent, or Firm—Adams & Wilks

(57) ABSTRACT

An ophthalmic apparatus has an illumination optical system for illuminating a preselected point of a patient's eye with slit-light. Objective lenses are each disposed in an observation optical path for forming an image of the preselected point of the patient's eye. Eyepiece systems are disposed in respective ones of the observation optical paths for observing the image of the preselected point of the patient's eye. An imaging device captures the image of the preselected point of the patient's eye. An optical element guides the image of the preselected point of the patient's eye to the imaging device. The optical element is disposed between the objective lenses at a position that does not lie in any of the observation optical paths.

22 Claims, 3 Drawing Sheets

OPHTHALMIC APPARATUS

BACKGROUND OF THE INVENTION

1. Field of the Invention

The present invention relates to an ophthalmic apparatus, and more particularly to a portable ophthalmic apparatus equipped with an illumination optical system for illuminating a specified point of a patient's eye with slit-light, and an observation optical system for observing an image of the illuminated point of the eye via eyepieces.

2. Description of the Prior Art

Portable ophthalmic apparatuses include portable slit-lamps used for observing the anterior portion of a patient's eye. Examples of such apparatuses are described in Japanese Utility Model Laid-Open Publication No. 24107/91 and Japanese Patent Laid-Open Publications Nos. 128036/91 and 164114/96. More recently, there are slit-lamps that can obtain electric images of the anterior portion of an eye.

With respect to ophthalmic apparatuses for observing the anterior part of an eye, it is desirable to be able to perform such observations using both eyes. Therefore, when the anterior portion is imaged electronically, the image optical path is split at the eyepiece part of the apparatus in prior arts. A problem with such an arrangement is that the observed image is degraded by a loss of light quantity and by the increase in the optical parts, and another problem is a difference between observed images and electronically captured images. One possible way around this is to capture the image from a different direction than the objective lens. However, the problem with this is that since the observed image and electronic image have different directions, it is difficult for the examiner conducting the examination to obtain the desired electronic images.

In the case of portable slit-lamps, there is also the problem of hand-movement that makes it difficult to obtain good images.

It is therefore an object of the invention to provide an ophthalmic apparatus that is able to reduce the difference between observed and captured images and can also obtain good observed images.

SUMMARY OF THE INVENTION

According to the present invention, an ophthalmic apparatus comprises an illumination optical system for illuminating a specified point of a subject eye with slit-light, an observation optical system including objective lenses for respectively forming an image of the specified point of the subject eye and left and right eyepiece systems for observing the image of the specified point with left and right eyes, an optical element disposed in a space that lies between the objective lenses and the specified point and between an effective diametric center of the left eyepiece system and an effective diametric center of the right eyepiece system, and an imaging device for capturing the image of the specified point which is guided thereto via the optical element.

An ophthalmic apparatus according to the invention includes a first unit and a second unit that can be detachably attached to the first unit. The objective lenses and left and right eyepiece systems are disposed in the first unit, and the optical element and the imaging device are disposed in the second unit.

With this arrangement, the optical member is located between the light path for left-eye observation and the light path for right-eye observation in order to guide the slit-image to the imaging device. This can substantially eliminate the differences between observed and captured images, and provide observation images with no degradation.

Further features of the invention, its nature and various advantages will be more apparent from the accompanying drawings and following detailed description of the invention.

DETAILED DESCRIPTION OF THE PREFERRED EMBODIMENT

Figure 1A:
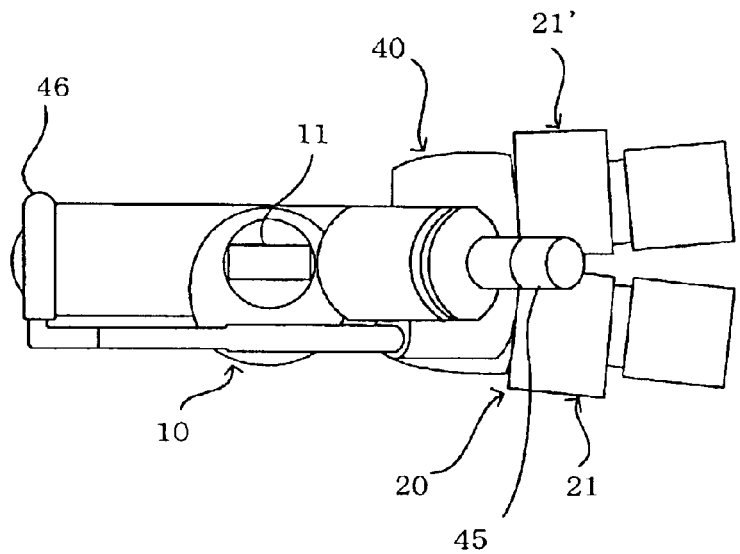
FIG. 1a is a top view showing an ophthalmic apparatus of the present invention.
Figure 1B:
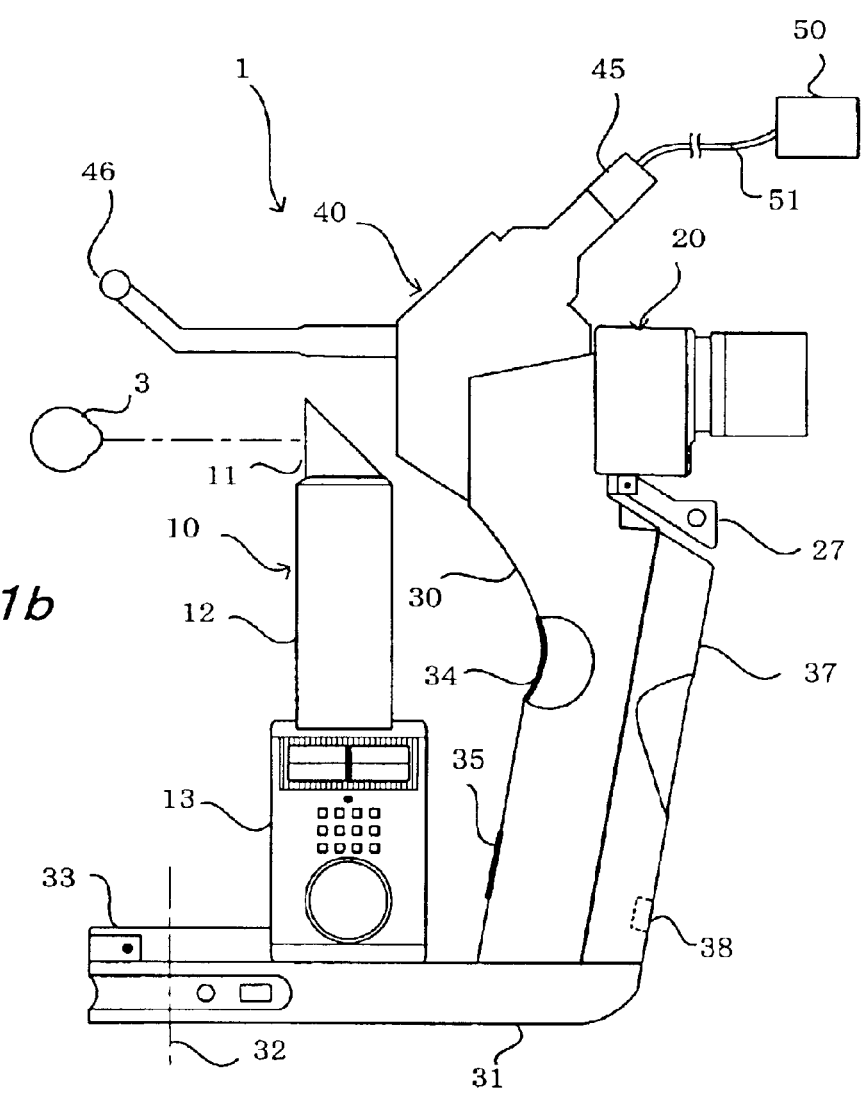
FIG. 1b is a side view showing an ophthalmic apparatus of the present invention.

Details of an embodiment of the present invention will now be described with reference to the drawings.

The example of the portable ophthalmic apparatus 1 shown in FIGS. 1a, 1b and 2a, 2b is a slit-lamp apparatus used in particular for examining the anterior portion of an eye. The apparatus 1 is composed of an optical illumination system 10 for illuminating the anterior portion of a subject eye 3 with slit-light, a first unit 20 having a grip portion 30 and constituting the observation optical system, and a second unit 40 that can be detachably attached to the first unit 20 and includes a CCD camera (imaging device) 45 used to capture and photoelectrically convert observed images of the anterior eye portion.

Figure 2A:
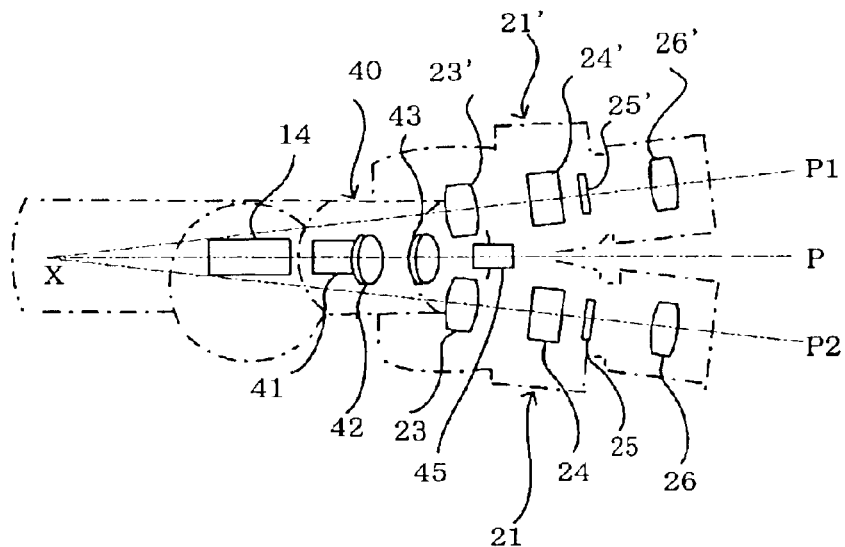
FIG. 2a is a top view showing the internal optical system of the ophthalmic apparatus.
Figure 2B:
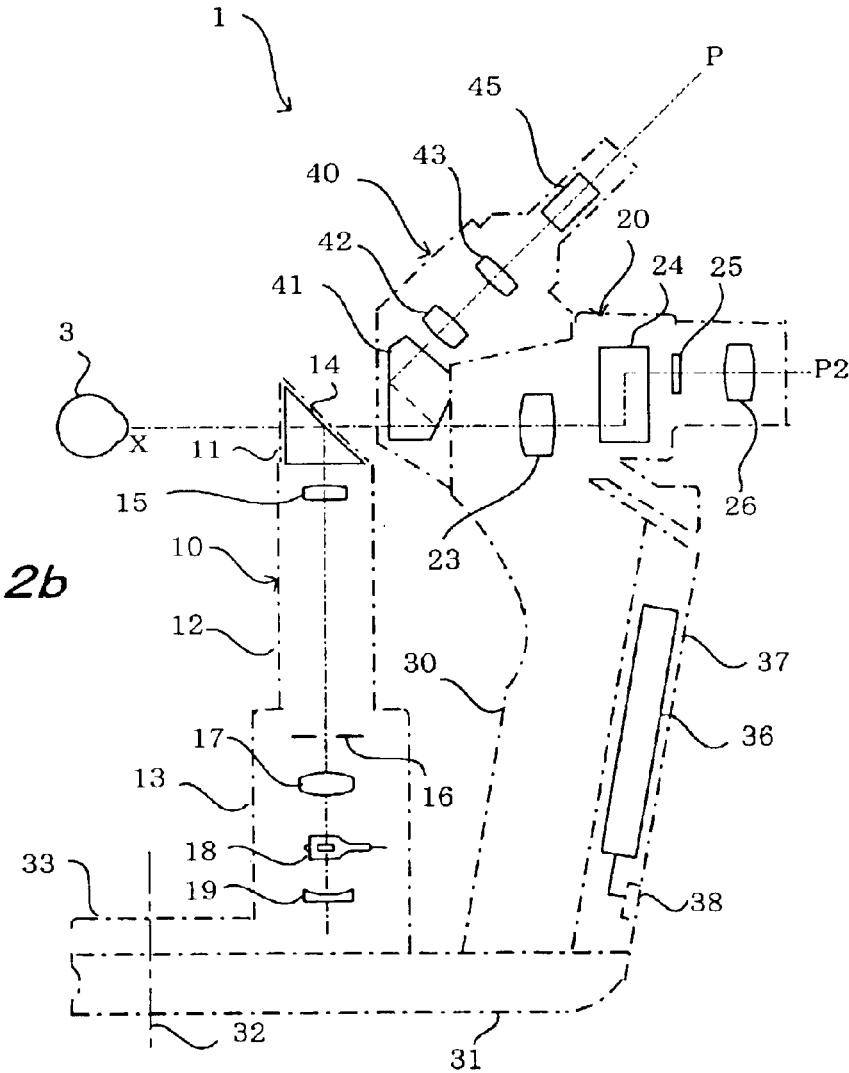
FIG. 2b is a side view showing the internal optical system of the ophthalmic apparatus.

The optical illumination system 10 comprises a slit projector 11, a projection lens barrel 12 that supports the slit projector 11, and a slit mechanism section 13 disposed below the projection lens barrel 12. As shown in FIGS. 2a and 2b, the slit projector 11 includes a slit projection prism 14, and the projection lens barrel 12 houses a projection lens 15. The slit mechanism section 13 includes, in order from the top, a slit 16, a condenser lens 17, a light source 18 and a reflector 19. The slit projection prism 14, projection lens 15, slit 16, condenser lens 17, light source 18 and reflector 19 provide an optical illumination system in which the slit 16 is used to project a slit-image onto specified point X of the eye 3 to illuminate the anterior portion of the eye.

The first unit 20 includes a left-eye observation section 21, a right-eye observation section 21' and a grip portion 30 which the examiner uses to hold the slit-lamp apparatus. An arm 31 is attached to the lower part of the grip portion 30, and an arm 33 is provided on the lower part of the optical illumination system 10 so as to pivot about the free end of the arm 31 by means of a spindle 32. Thus, the arms 33 and 31 enable the optical illumination system 10 and first unit 20 to be swung relative to each other about the spindle 32.

As shown in FIGS. 2a and 2b, the left-eye observation section 21 includes an observation optical system constituted by an objective lens 23 and a left-eyepiece system comprising an erecting prism 24, a reticule 25 and an eyepiece 26. The right-eye observation section 21' includes an observation optical system constituted by an objective lens 23' and a right-eyepiece system comprising an erecting prism 24', a reticule 25' and an eyepiece 26'. Optical axes P1 and P2 from the eye 3 pass through the respective objective lenses 23 and 23' and the erecting prisms 24 and 24', which then deflect the optical axes through the reticules 25 and 25' and eyepieces 26 and 26'. The objective lenses 23 and 23' respectively form an image of the anterior portion of the eye 3 illuminated by the slit-light. The left-eyepiece and right-eyepiece systems enable the examiner to observe the image of the anterior portion of the eye 3 with both eyes. The objective lenses 23 and 23' can be moved along the light axis by a lever 27 to change the image magnification factor. When the second unit 40 is attached to the first unit 20, the lever 27 is locked to prevent the objective lenses 23 and 23' from being moved.

Figure 3:
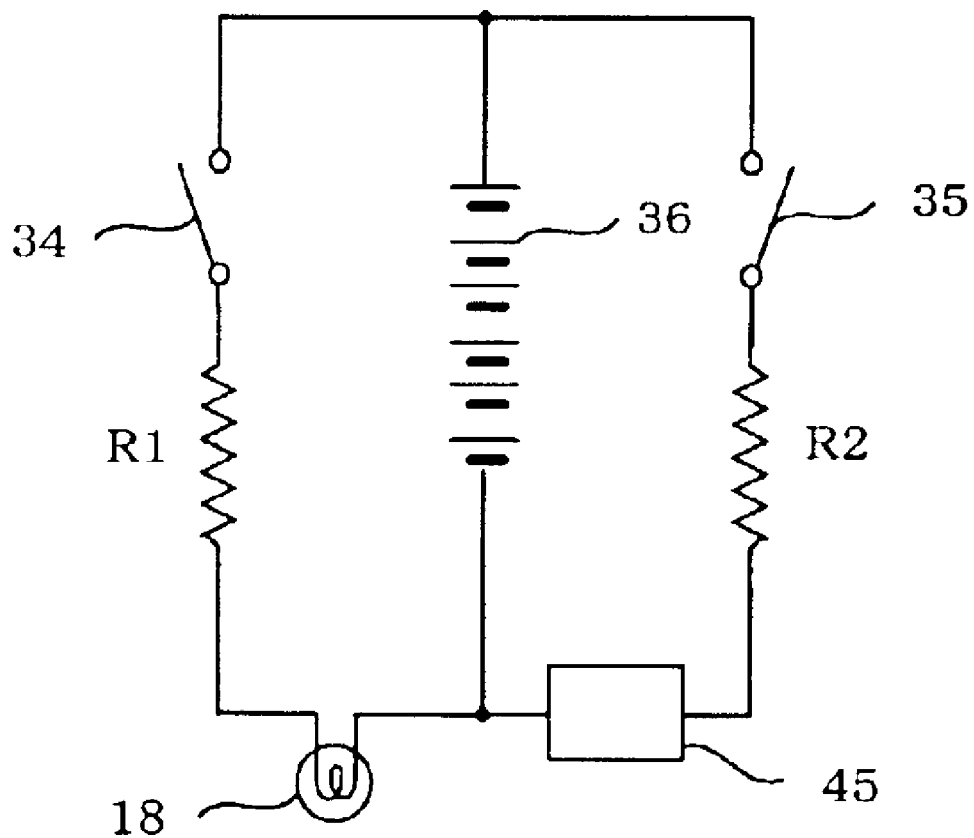
FIG. 3 is a diagram showing the circuit used to supply electricity from an internal battery.

The grip portion 30 has a power supply compartment 37 that contains a power supply comprised of a battery 36. As shown in the equivalent circuit in FIG. 3, the battery 36 is connected to the light source 18 via a resistor R1 and a switch 34 provided on the grip portion 30. When the examiner uses the switch 34 to turn on the light source 18, the slit 16 is illuminated by the light source 18 to produce slit-light. The grip portion 30 is provided with terminals 38 for charging the battery 36. The battery 36 is also connected to the CCD camera 45 via a resistor R2 and a switch 35 provided on the grip portion 30. The operation of the switch 35 enables the CCD camera 45 to be supplied with electricity.

The second unit 40 has a reflecting member 41 for reflecting the slit-image from the eye 3 to the CCD camera 45, imaging lenses 42 and 43, and the CCD camera 45 that functions as the imaging device. The reflecting member 41 is an optical element such as a mirror, half-mirror or prism or the like, and is located in the space between the objective lens 23 (23') and the specified point X of the eye 3 and between the effective diametric center of the left eyepiece system and the effective diametric center of the right eyepiece system, that is, between the light paths of the left and right observation optical systems. Depending on its location, the reflecting member 41 may cut part of the image to be produced by the objective lens 23 and 23', but when the amount involved is small, it does not affect the quality of the observed image. However, it is preferable to adjust the positions of the reflecting member 41 and objective lens 23 and 23' so as to prevent any cutting of the image.

The reflecting member 41 causes the light axis P from the eye 3 to be inclined upwards to pass through lenses 42 and 43 to the CCD camera 45. The slit-image of the anterior portion is formed on the CCD camera 45 and captured by it. The image thus captured by the CCD camera 45 can be recorded in an external storage device 50 such as a hard disk, flash memory or the like, via a cable 51.

The second unit 40 is also provided with a forehead rest 46, against which the patient presses his forehead to keep the position of the point X of the eye 3 steady. The second unit 40 is provided with means (not shown) for pressing the forehead rest in the direction of the subject eye.

The operation of the ophthalmic apparatus will be described in the following.

When the anterior portion of the eye is to be imaged, the second unit 40 is attached to the first unit 20. The examiner grips the grip portion 30, aligns the slit projector 11 with the patient's eye 3 and uses the switch 34 to switch the light source 18 on to illuminate the specified point X of the eye with slit-light. For positional steadiness at this time, the patient's forehead is pressed against forehead rest 46.

The slit-light can be projected from any direction by pivoting about spindle 32 the arm 31 attached to the lower part of the grip portion 30 and the arm 33 attached to the lower part of the optical illumination system 10. This enables an image of the illuminated anterior portion of the eye to be formed by the objective lens 23 and 23', while at the same time the right and left eyepiece systems allow the examiner to observe the image with both eyes.

The observed image can be captured by operating the switch 35 on the grip portion. This operation causes the CCD camera 45 to be activated by electrical power from the battery 36, and enables it to capture the slit-image of the anterior portion of the eye incident thereon via the reflecting member 41. Since the reflecting member 41 is located between the light paths of the left and right observation optical systems, that is, between the effective diametric centers of the left and right eyepiece systems, there is almost no difference between the image captured by the CCD camera 45 and the image seen by the examiner via the left and right observation optical systems. Also, since the observation optical system is not affected by the imaging optical system, there is no degradation in the quality of the observed images.

The images captured by the CCD camera 45 can be recorded in the storage device 50 for later replay. Instead of using an external storage device, the images can be recorded using a storage means provided in the second unit. This enables the cable 51 to be eliminated.

When the apparatus is to be used not for imaging but only for observation, the second unit 40 is detached from the first unit. This also removes the forehead rest 46, reducing the weight of the ophthalmic apparatus when used just for observation. When a video recording of the images is required, the forehead rest 46 can be readily attached to ensure the steadiness of the positional relationship, making it possible to provide images of good quality.

When the second unit 40 is attached to the first unit 20 for video imaging, the lever 27 is locked and the objective lens 23 (23') is prevented from being moved. This prevents the magnification factor of the observed images being inadvertently changed during the imaging, thereby keeping the imaging and observation ranges matched. Also, an arrangement can be used whereby the position (magnification factor) at which the objective lens 23 (23') is locked by the lever 27 depends on the size of the imaging area of the CCD camera 45.

As described in the foregoing, the invention makes it possible to capture a slit-image of a specified point of an eye illuminated by slit-light via an optical element that is disposed between the image-forming objective lens and the specified point and between the effective diametric center of the left eyepiece system and the effective diametric center of the right eyepiece system. This enables differences between the observed and captured images to be substantially eliminated and the images to be observed with no degradation.

What is claimed is:

1. An ophthalmic apparatus comprising:
   an illumination optical system for illuminating a specified point of a patient's eye with slit-light;
   an observation optical system having objective lenses for forming an image of the specified point of the patient's eye, and left and right eyepiece systems through which an examiner observes the image of the specified point of the patient's eye with left and right eyes, respectively;
   an optical element disposed in a space that lies between the objective lenses of the observation optical system and the specified point of the patient's eye and between an effective diametric center of the left eyepiece system and an effective diametric center of the right eyepiece system; and an imaging device for capturing the image of the specified point of the patient's eye via the optical element.

2. An ophthalmic apparatus according to claim 1; further comprising a first unit and a second unit for removable connection to the first unit, the objective lenses and the left and right eyepiece system of the observation optical system being disposed in the first unit and the optical element and the imaging device being disposed in the second unit.

3. An ophthalmic apparatus according to claim 2; wherein the second unit has a forehead rest for supporting the forehead of the patient to maintain a steady positional relationship with the specified point of the patient's eye.

4. An ophthalmic apparatus according to claim 3; wherein the second unit includes means for pressing the forehead rest in the direction of the patient's eye.

5. An ophthalmic apparatus according to claim 2; wherein the objective lenses are configured to undergo movement along respective optical axes to vary an image magnification factor and are configured to be prevented from undergoing movement along the respective optical axes when the second unit is connected to the first unit.

6. An ophthalmic apparatus according to claim 5; wherein the objective lenses are configured to be locked at a preselected non-moving position in accordance with a size of an imaging area of the imaging device.

7. An ophthalmic apparatus according to claim 2; wherein the first unit has a grip to enable the examiner to manipulate the first unit.

8. An ophthalmic apparatus according to claim 7; wherein the grip has a switch for activating the imaging device.

9. An ophthalmic apparatus according to claim 2; wherein the illumination optical system has a slit-light source for producing the slit-light; and wherein the first unit has a power supply for supplying electricity to the slit-light source.

10. An ophthalmic apparatus according to claim 9; wherein the power supply comprises a rechargeable power supply.

11. An ophthalmic apparatus according to claim 9; wherein the power supply supplies electricity to the imaging device.

12. An ophthalmic apparatus according to claim 2; further comprising a storage apparatus disposed in the second unit for storing the image captured by the imaging device.

13. An ophthalmic apparatus according to claim 2; further comprising a storage apparatus for storing the image captured by the imaging device and configured to be connected to the second unit.

14. An ophthalmic apparatus comprising:

a light source for producing slit-light;

an illumination system for illuminating a preselected point of a patient's eye with the slit-light produced by the light source;

a pair of objective lenses each disposed in an observation optical path for forming an image of the preselected point of the patient's eye illuminated with the slit-light;

a pair of eyepiece systems disposed in respective ones of the observation optical paths for observing the image of the preselected point of the patient's eye formed by the objective lenses;

an imaging device for capturing the image of the preselected point of the patient's eye formed by the objective lenses; and an optical element for directing the image of the preselected point of the patient's eye formed by the objective lenses to the imaging device, the optical element being disposed between the objective lenses and the preselected point of the patient's eye at a position that does not lie in any of the observation optical paths.

15. An ophthalmic apparatus according to claim 14; wherein the optical element is disposed between effective diametric centers of the eyepiece systems.

16. An ophthalmic apparatus according to claim 14; wherein the optical element is disposed between the observation optical paths.

17. An ophthalmic apparatus according to claim 14; further comprising a first unit having the objective lenses and the eyepiece systems, and a second unit removably connected to the first unit and having the imaging device and the optical element.

18. An ophthalmic apparatus comprising:

a light source for producing slit-light;

an illumination system for illuminating a preselected point of a patient's eye with the slit-light produced by the light source;

a pair of objective lenses each disposed in an observation optical path for forming an image of the preselected point of the patient's eye illuminated with the slit-light;

a pair of eyepiece systems each disposed in respective ones of the observation optical paths for observing the image of the preselected point of the patient's eye formed by the objective lenses;

an imaging device for capturing the image of the preselected point of the patient's eye formed by the objective lenses; and optical means for guiding the image of the preselected point of the patient's eye formed by the objective lenses to the imaging device, the optical means being positioned relative to the eyepiece systems so that no differences exist between the image of the preselected point of the patient's eye observed via the eyepiece systems and the image of the preselected point of the patient's eye captured by the imaging device.

19. An ophthalmic apparatus according to claim 18; wherein the optical means is disposed between effective diametric centers of the eyepiece systems.

20. An ophthalmic apparatus according to claim 18; wherein the optical means is disposed between the observation optical paths.

21. An ophthalmic apparatus according to claim 18; wherein the optical means is disposed at a position that does not lie in any of the observation optical paths.

22. An ophthalmic apparatus according to claim 18; further comprising a first unit having the objective lenses and the eyepiece systems and a second unit removably connected to the first unit and having the imaging device and the optical means.

* * * * *